(12) United States Patent
Cambronne et al.

(10) Patent No.: US 11,110,264 B2
(45) Date of Patent: Sep. 7, 2021

(54) INTRAVASCULAR PUMP WITH EXPANDABLE DISTAL REGION

(71) Applicant: Cardiovascular Systems, Inc., St. Paul, MN (US)

(72) Inventors: Matthew D. Cambronne, North Oaks, MN (US); Joseph P. Higgins, Minnetonka, MN (US); Benjamin D. Haselman, St. Paul, MN (US); Tristan A. Van de Moortele, Minneapolis, MN (US); Matthew W. Tilstra, Rogers, MN (US); Jeffrey R. Stone, Minnetonka, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 158 days.

(21) Appl. No.: 16/388,362

(22) Filed: Apr. 18, 2019

(65) Prior Publication Data
US 2019/0321530 A1    Oct. 24, 2019

Related U.S. Application Data

(60) Provisional application No. 62/660,538, filed on Apr. 20, 2018, provisional application No. 62/660,511, filed on Apr. 20, 2018.

(51) Int. Cl.
*A61M 60/205* (2021.01)
*A61M 60/135* (2021.01)
(Continued)

(52) U.S. Cl.
CPC ........ *A61M 60/205* (2021.01); *A61M 60/135* (2021.01); *A61M 60/148* (2021.01);
(Continued)

(58) Field of Classification Search
CPC .. A61M 1/1024; A61M 1/1031; A61M 1/122; A61M 1/125; A61M 1/1008; A61M 1/1012; A61M 1/101; A61M 2205/0266
See application file for complete search history.

(56) References Cited

U.S. PATENT DOCUMENTS

| 6,544,216 B1 | 4/2003 | Sammler et al. |
| 2004/0044266 A1* | 3/2004 | Siess ................. A61M 25/0662 600/16 |

(Continued)

OTHER PUBLICATIONS

International Preliminary Report on Patentability issued in related PCT Application No. PCT/US2019/028262, dated Oct. 20, 2020.

(Continued)

*Primary Examiner* — William J Levicky
*Assistant Examiner* — Alexander M Eisenberg
(74) *Attorney, Agent, or Firm* — Barnes & Thornburg LLP; Jeffrey R. Stone

(57) ABSTRACT

The present invention provides an intravascular blood pump comprising an expandable and collapsible region distal to a pump assembly. In some embodiments, the expandable and collapsible region may comprise expandable and collapsible proximal and/or distal transition sections adjacent a central expandable and collapsible region. Support structure, e.g., an expandable and collapsible stent may comprise at least a part of the expandable and collapsible region. In some embodiments, a distal portion of the housing comprises the expandable and collapsible region, wherein an inversion of the distal housing results in a collapsed configuration and eversion of the distal housing results in an expanded configuration.

17 Claims, 6 Drawing Sheets

(51) Int. Cl.
*A61M 60/148* (2021.01)
*A61M 60/422* (2021.01)
*A61M 60/857* (2021.01)

(52) U.S. Cl.
CPC ........ *A61M 60/422* (2021.01); *A61M 60/857* (2021.01); *A61M 2205/0266* (2013.01)

(56) References Cited

U.S. PATENT DOCUMENTS

| | | |
|---|---|---|
| 2008/0132747 A1 | 6/2008 | Shifflette |
| 2008/0132748 A1* | 6/2008 | Shifflette ............. A61M 60/205 600/16 |
| 2008/0262337 A1* | 10/2008 | Falwell .............. A61B 18/1492 600/374 |
| 2011/0004046 A1 | 1/2011 | Campbell et al. |
| 2013/0303831 A1 | 11/2013 | Evans |
| 2014/0107399 A1* | 4/2014 | Spence ................. A61M 1/122 600/16 |
| 2014/0200395 A1* | 7/2014 | Shafi ....................... A61L 31/06 600/37 |

OTHER PUBLICATIONS

International Search Report and Written Opinion issued in related PCT Application No. PCT/US2019/028262, dated Jul. 10, 2019.

* cited by examiner $D_1 > D_2$

INTRAVASCULAR PUMP WITH EXPANDABLE DISTAL REGION

CROSS-REFERENCE TO RELATED APPLICATIONS

This application claims the benefit of provisional application 62/660,538, filed Apr. 20, 2018 and entitled INTRAVASCULAR PUMP WITH EXPANDABLE REGION—INVERTED, BLOOMING, CAP, CAGE and provisional application 62/660,511, filed Apr. 20, 2018 and entitled INTRAVASCULAR BLOOD PUMP WITH EXPANDABLE REGION, the contents of which are hereby incorporated by reference in their entirety.

STATEMENT REGARDING FEDERALLY SPONSORED RESEARCH OR DEVELOPMENT

Not Applicable

BACKGROUND OF THE INVENTION

Field of the Invention

The invention relates to an intravascular pump with an expandable region disposed distal to the impeller assembly.

Description of the Related Art

With reference to FIG. 1, the human heart comprises four chambers and four heart valves that assist in the forward (antegrade) flow of blood through the heart. The chambers include the left atrium, left ventricle, right atrium and left ventricle. The four heart valves include the mitral valve, the tricuspid valve, the aortic valve and the pulmonary valve.

The mitral valve is located between the left atrium and left ventricle and helps control the flow of blood from the left atrium to the left ventricle by acting as a one-way valve to prevent backflow into the left atrium. Similarly, the tricuspid valve is located between the right atrium and the right ventricle, while the aortic valve and the pulmonary valve are semilunar valves located in arteries flowing blood away from the heart. The valves are all one-way valves, with leaflets that open to allow forward (antegrade) blood flow. The normally functioning valve leaflets close under the pressure exerted by reverse blood to prevent backflow (retrograde) of the blood.

Thus, as illustrated, the general blood flow comprises deoxygenated blood returning from the body where it is received by the right atrium via the superior and inferior vena cava and is, in turn, pumped into the right ventricle, a process controlled by the tricuspid valve. The right ventricle functions to pump the deoxygenated blood to the lungs via the pulmonary arteries, where the blood is reoxygenated and returned to the left atrium via the pulmonary veins.

Heart disease is a health problem with a high mortality rate. The use of temporary mechanical blood pump devices are used on an increasingly frequent basis to provide short-term acute support during surgery or as temporary bridging support to help a patient survive a crisis. These temporary blood pumps have developed and evolved over the years to supplement the pumping action of the heart on a short-term basis and supplement blood flow as either left or right ventricular assist devices, with the left ventricular assist device ("LVAD") currently the most commonly used device.

Known temporary LVAD devices generally are delivered percutaneously, e.g., through the femoral artery, to locate or position the LVAD inlet in the patient's left ventricle and the outlet in the patient's ascending aorta with the body of the device disposed across the aortic valve. As the skilled artisan will understand, an incision may be made below the patient's groin to enable access to the patient's femoral artery. The physician may then translate guide wire, followed by a catheter or delivery sheath, through the femoral artery and descending aorta until reaching the ascending aorta. The LVAD with attached rotational drive shaft may then be translated through the delivery catheter or sheath lumen, leaving a proximal end of the drive shaft exposed outside of the patient and coupled with a prime mover such as an electric motor or the equivalent for rotating and controlling the rotational speed of the drive shaft and associated LVAD impeller.

Temporary axial flow blood pumps consist generally of two types: (1) those that are powered by a motor integrated into the device that is connected with the pump's impeller (see U.S. Pat. Nos. 5,147,388 and 5,275,580); and (2) those that are powered by an external motor that provides rotational torque to a drive shaft which is, in turn, connected to the pump's impeller (see U.S. Pat. No. 4,625,712 to Wampler and U.S. Pat. No. 5,112,349 to Summers, each hereby incorporated by reference in their entirety).

Known temporary ventricle assist devices ("VAD"), including LVAD and RVAD (right ventricular assist) devices, whether with integrated motor or an external motor, generally comprise the following elements mounted within a housing, listed in order from the inflow end to the outflow end: an inflow aperture(s); a stationary inducer, also known as a flow straightener; a rotational impeller; and a stationary diffuser and/or outflow structure; and an outflow aperture(s) as shown in the exemplary prior art pump and/or impeller assembly cross sectional and cutaway view of FIG. 2.

In FIG. 2, the known device 2 is oriented with the inflow end (distal end) on the left side of the drawing and the outflow end (proximal) on the right side, so that the incoming blood flow in the ventricle enters the device housing through the inflow aperture(s) (not shown), flows through the defined by the surrounding housing 14, ultimately entering the impeller/pump assembly 4. There, the incoming blood encounters the stationary inducer 6 before being urged forward by the rotating impeller 8. The blood flow may then be modified by a stationary diffuser and exits into the aorta via the housing's outflow aperture(s) 10.

Known VAD or LVAD devices further comprise a delivery configuration and a functional or working configuration, with the delivery configuration having a lower profile or smaller diameter than the functional or working configuration to, inter alia, facilitate atraumatic delivery through a delivery sheath. Stated differently, through various means the housing of the VAD or LVAD, and/or the blades of the impeller, may expand to achieve the functional or working configuration and collapse to achieve the delivery configuration. However, known devices collapse and expand the impeller blades and/or the housing wherein the collapsible and expandable housing surrounds at least a portion of the impeller in order to enable moving between an expanded or working configuration and/or require an integrated motor proximate the impeller. See, e.g., U.S. Pat. Nos. 7,027,875; 7,927,068; and 8,992,163.

Known LVAD devices will typically comprise an angled housing to accommodate the aortic arch, the angle or bend generally in the range of 135 degrees.

LVAD devices with integrated motors within the housing must be small enough to allow atraumatic intravascular translation and positioning within the heart. Though various means are known to collapse portions of the device while within the catheter or delivery sheath, including the housing and/or the impeller or parts thereof such as the blades, the size of the collapsed device may be limited by the integrated motor.

In addition, the known LVAD devices comprise a delivery configuration wherein the housing and/or impeller, e.g., the blades on the impeller, may be reduced in diameter and, when delivered distally from the delivery catheter or sheath, the collapsed elements are enabled to expand. These devices are limited in several respects. First, the collapsing and expanding comprises at least a portion of the housing that is occupied by the impeller. Second, the inflow region of the housing, that is the region distal to the rotational impeller and the stationary inducer or flow straightener, comprises an area of opportunity to optimize blood flow through the cannula or housing. Known LVAD or VAD devices do not take advantage of this opportunity. Third, known LVAD or VAD devices comprise a stationary inducer or flow straightener encountered by blood upon entry into the pump which can contribute to, inter alia, thrombosis and/or hemolysis.

Various embodiments of the present invention address these, inter alia, issues.

The figures and the detailed description which follow more particularly exemplify these and other embodiments of the invention.

DETAILED DESCRIPTION OF THE INVENTION

Generally, various embodiments of the present invention are directed to mechanical assist devices for pumping blood in a patient. Improved temporary LVAD or VAD blood pumps are described herein that are delivered percutaneously and intravascularly.

Figure 1:
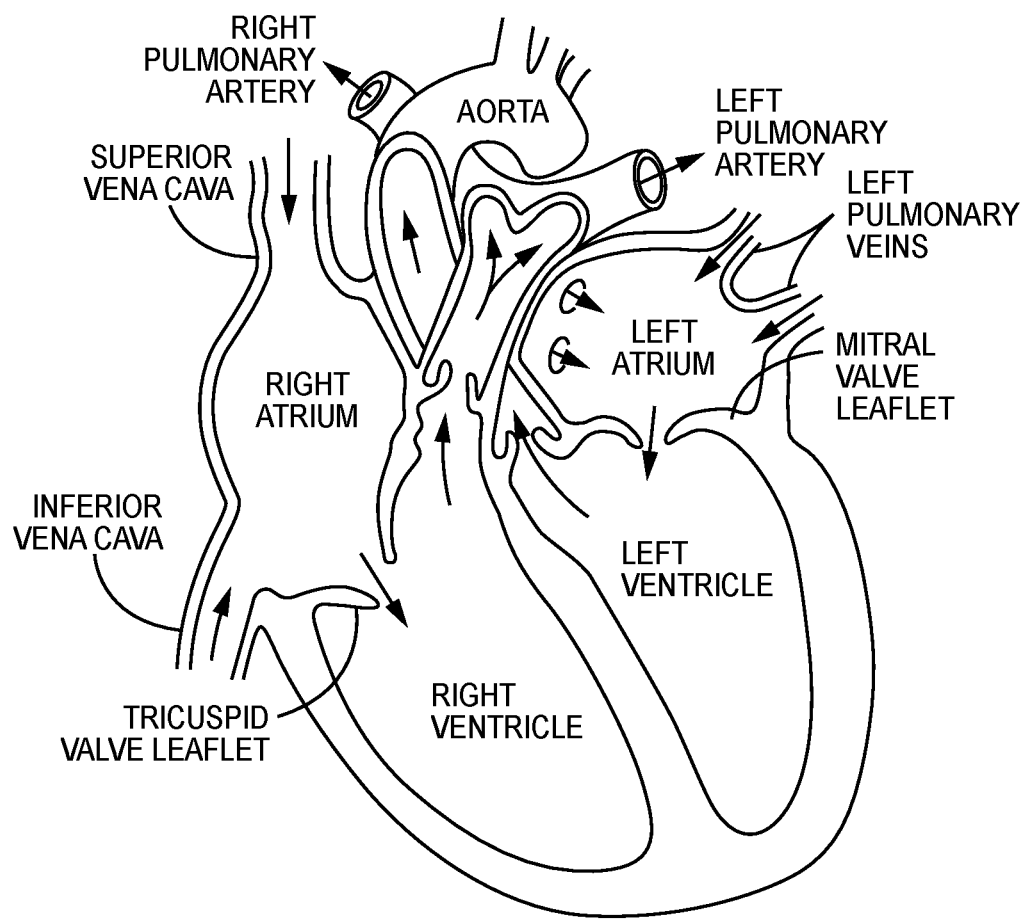
FIG. 1 is a cutaway view of the human heart.
Figure 2:
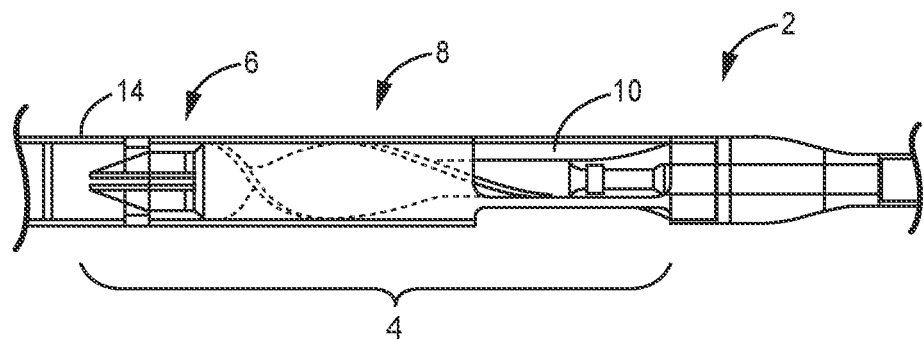
FIG. 2 is a cross-sectional view of a prior art device.
Figure 3:
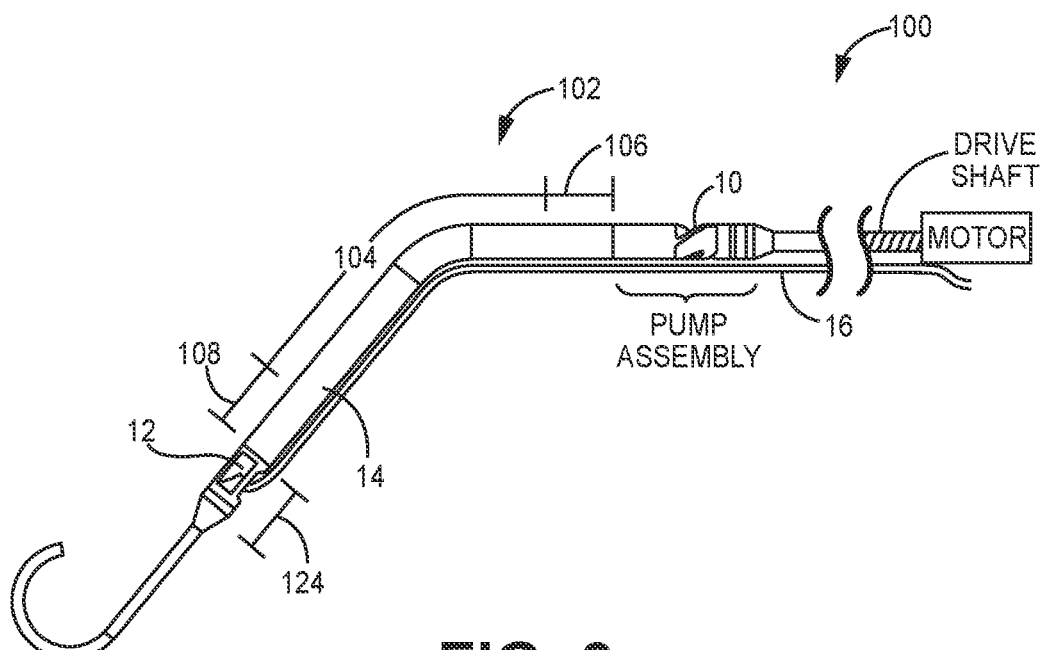
FIG. 3 is a side cutaway view of one embodiment of the present invention.

Referring now to FIG. 3, an exemplary LVAD blood pump 100 is illustrated, with inflow apertures 12 on the left side of the illustration and outflow apertures 10 on the right side of the device.

The entire length of outer housing 14 is shown as comprising a relatively constant diameter from the inlet or inflow apertures 12 to the outlet or outflow apertures 10. Guide wire 16 is positioned alongside the exterior of the device until reaching the inlet apertures 12 where it enters the lumen of cannula C and extends distally therefrom as shown. Thus, the guide wire 16 does not pass through the impeller or rotor 8 (not visible in FIG. 3) or pump assembly. The configuration shown in FIG. 3 may comprise a delivery configuration with an expandable region 102 compressed within an introducer or delivery sheath or catheter 200 (See FIGS. 5A, 5B, 9, 13A and 16-19).

With reference generally to the Figures, the device 100 may comprise an expandable region 102 that may be located distal to the impeller or rotor or pump assembly, such that the housing diameter surrounding the impeller or rotor or pump assembly does not change diameter during delivery or during rotation. Stated differently, a proximal non-expandable region 122 may be provided and comprises at least the impeller or rotor or pump assembly and the housing surrounding that assembly does not expand or contract appreciably but may be flexible. Further, a distal non-expandable region 124 may also be provided comprising at least the inlet region including at least the inlet apertures 12. Thus, the expandable region 102 comprises a proximal end and a distal end. The proximal end of the expandable region 102 abuts or is adjacent to a distal end of the proximal non-expandable region 122 while the distal end of the expandable region 102 abuts or is adjacent to a proximal end of the distal non-expandable region 124. The housing H surrounding the non-expandable region(s) 122, 124 may, however, be flexible or pliable, but they are not disposed to a biased expansion.

Figure 4:
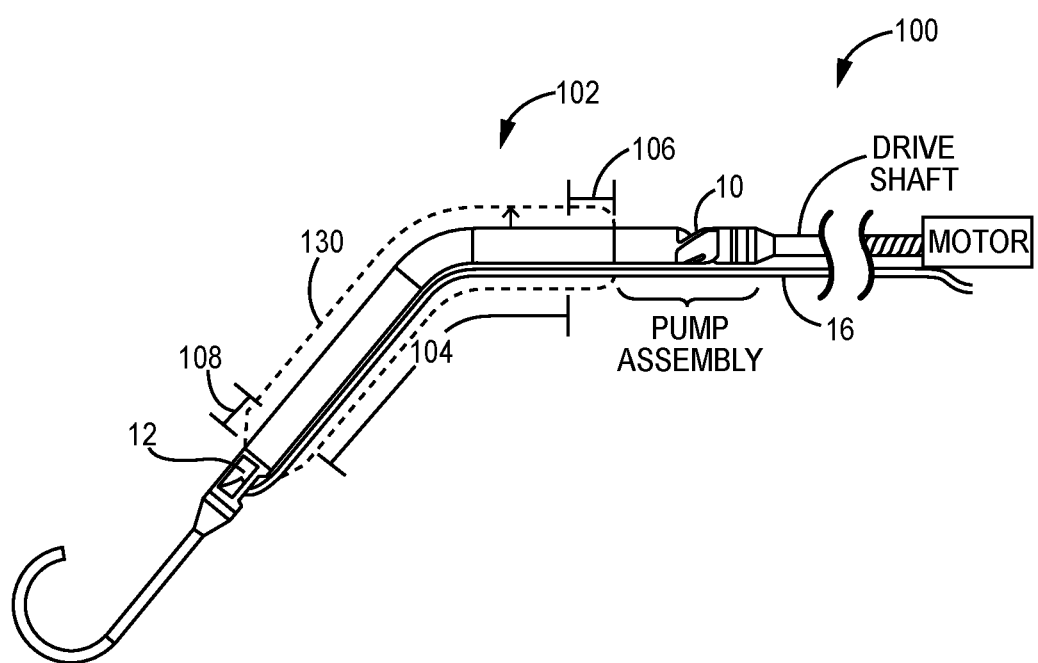
FIG. 4 is a side cutaway view of one embodiment of the present invention.

Thus, FIG. 4 shows device 100 and in dashed lines the change in diameter to/from a collapsed, deformed expandable region to an exemplary expanded undeformed expandable region, extending distally from a point distal to the end of the impeller, rotor and/or pump assembly along the hollow cannula to a point just proximal of the inlet apertures. The expandable region 102 may expand to a maximum undeformed diameter within the range of 12-20 Fr, more preferably between 16-20 Fr. In contrast, the unexpanded region remains at a substantially fixed diameter within the range of 9 to 12 Fr.

With continued reference to FIGS. 3 and 4, and the remaining Figures generally, the device 100 comprises an expandable region 102 that may be, either partially or completely, biased to the expanded configuration and, therefore, comprise a material or structure that facilitates expansion and may be biased to expand. Exemplary construction of the expandable region 102 may comprise a support structure 130 that is surrounded by an outer material, e.g., a jacket or coating or sleeve comprised of a plastic or polymeric material that accommodates an expansion of the underlying support structure as is known in the art. The support structure 130 may be formed of a shape memory material, for example Nitinol or similar. Other materials may comprise gold, tantalum, stainless steel, metal alloys, aerospace alloys and/or polymers including polymers that expand and contract upon exposure to relative heat and cold.

In other cases, at least a portion of the expandable region 102, e.g, a central expandable section 104 discussed infra, may comprise a polymeric or other material sleeve that is configured to allow and/or accommodate expansion and collapsing and a support structure 130 may be omitted. FIG. 4 provides a rotational drive shaft connected with the impeller assembly and is, in turn, connected with a prime mover such as an electric motor that is located outside the patient's body. It will be understood, however, that the various embodiments of the inventions discussed herein may also be used in combination with blood pumps comprising motors integrated therein, i.e., no external motor.

Figure 5A:
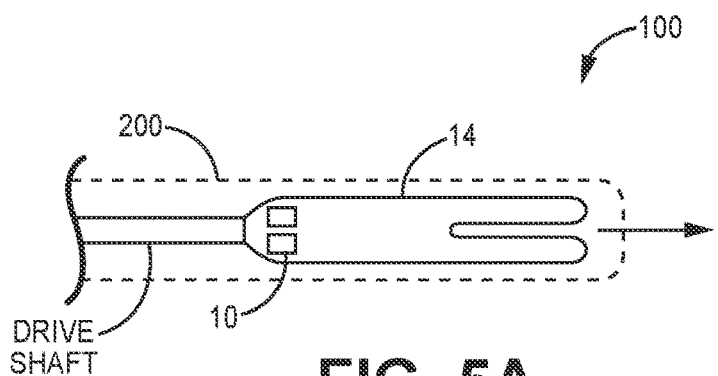
FIG. 5A is a side cutaway view of one embodiment of the present invention.
Figure 5B:
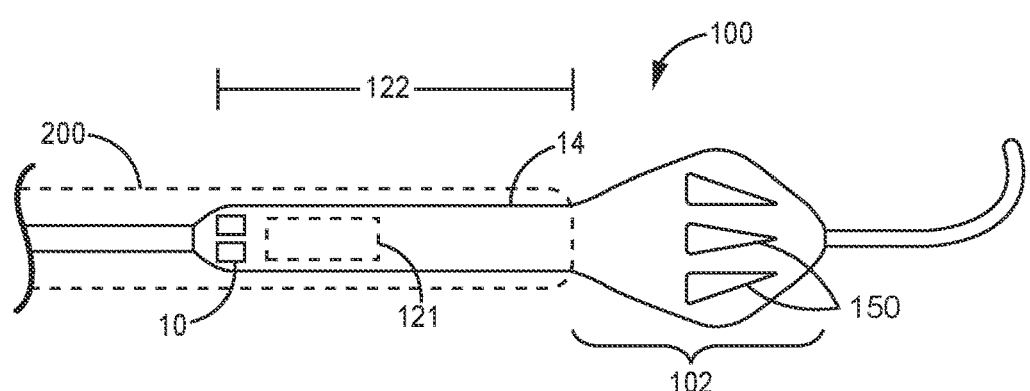
FIG. 5B is a side cutaway view of one embodiment of the present invention.
Figure 5C:
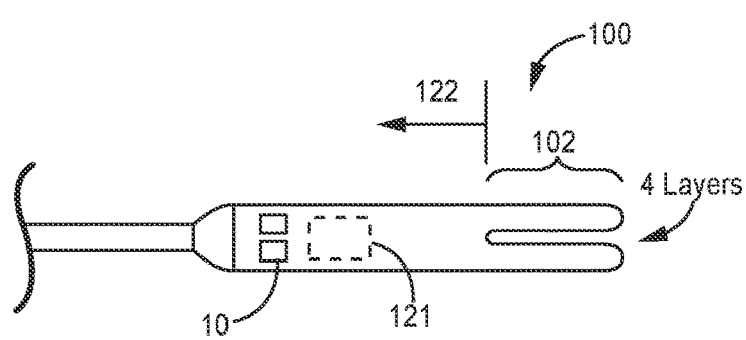
FIG. 5C is a side cutaway view of one embodiment of the present invention.
Figure 5D:
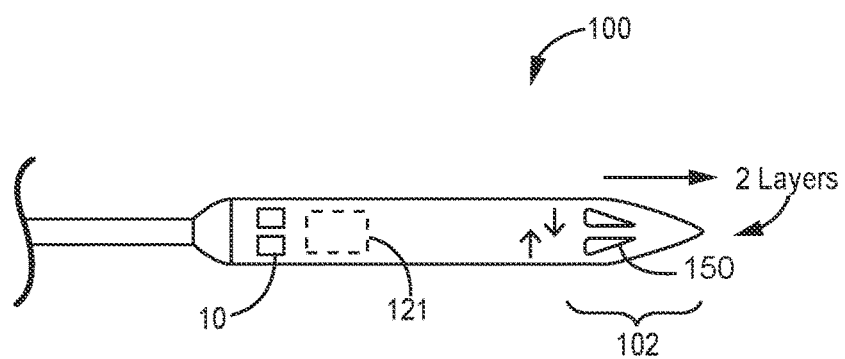
FIG. 5D is a side cutaway view of one embodiment of the present invention.
Figure 6A:
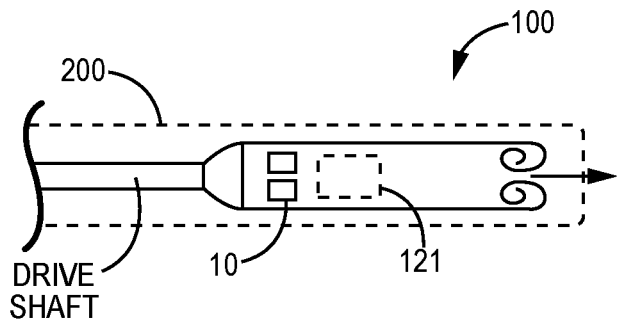
FIG. 6A is a side cutaway view of one embodiment of the present invention.
Figure 6B:
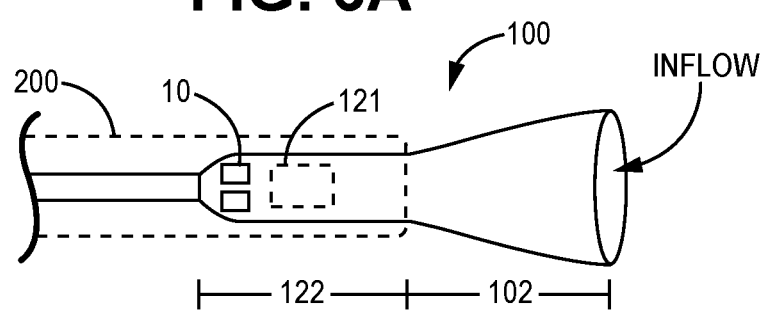
FIG. 6B is a side cutaway view of one embodiment of the present invention.
Figure 6C:
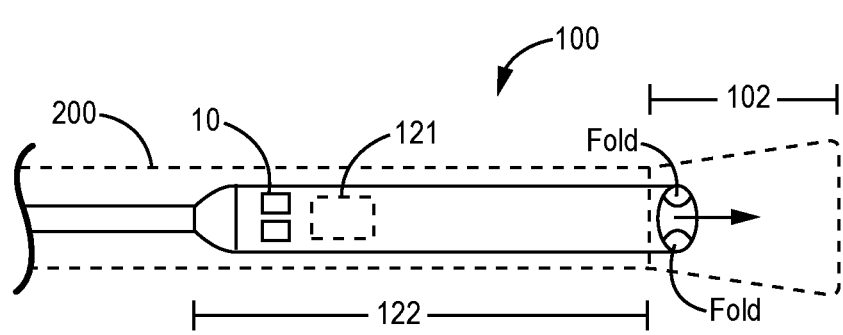
FIG. 6C is a side cutaway view of one embodiment of the present invention.
Figure 7:
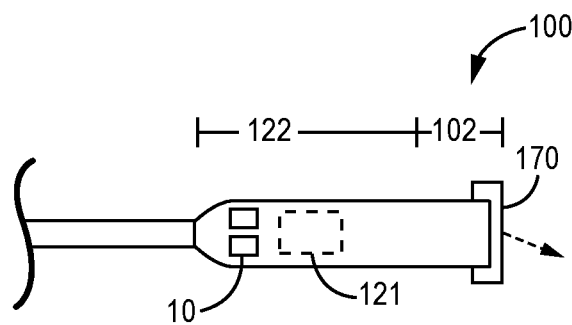
FIG. 7 is a side cutaway view of one embodiment of the present invention.

In many of the embodiments described herein, e.g., FIGS. 5A-5D, 6A-6C and in some cases FIG. 7, the expandable region 102 may comprise a single expandable region, without need or reason to distinguish between a proximal transition section, central expandable section and/or distal transition section.

Generally, the expandable region 102 of the present invention may comprise a support structure 130 surrounded by a polymer coating or jacket that adapts to expansion and collapsing of the expandable region 102.

Further, the support structure 130 may comprise an expandable stent-like structure formed of a series of cells formed from interacting and/or interconnected wires and/or struts and that enable collapsing and biased expansion of a structure, e.g., a stent, as is known in the art. For example, see U.S. Pat. No. 5,776,183 to Kanesaka; U.S. Pat. No. 5,019,090 to Pinchuk; U.S. Pat. No. 5,161,547 to Tower; U.S. Pat. No. 4,950,227 to Savin; U.S. Pat. No. 5,314,472 to Fontaine; U.S. Pat. Nos. 4,886,062 and 4,969,458 to Wiktor; and U.S. Pat. No. 4,856,516 to Hillstead, the disclosures of each of which are hereby incorporated in their entirety by reference.

As illustrated in FIGS. 3 and 4, the expandable region 102 may comprise a single region of expandability and collapsing.

Turning specifically to FIGS. 5A-5D, the device 100 is shown (straightened relative to that of FIGS. 3 and 4) collapsed within the lumen of an introducer sheath or delivery catheter 200. The expandable section 102 is in FIG. 5A at least partially inverted within the outer walls of the housing 14 to accommodate a lower profile during delivery. In this embodiment, as in FIG. 5B, the inverted portion may be returned to the everted form. The eversion may be achieved in a number of ways. First, the impeller may be operated in a retrograde or reverse flow direction to force blood flow through the inverted section with a force sufficient to cause eversion. Second, native blood flow during diastole may be sufficient to cause eversion of the inverted section. Further, a push wire may be delivered that may be used to press distally against the inverted section to generate enough force to cause eversion. In this connection, the guide wire may comprise a raised area that limits its distal travel with regard to the lumen in the housing 14 so that pushing the guide wire against the everted section's distal aperture defining the distal end of the housing lumen may urge the inverted section to become everted. Finally, extension of the expandable region 102 outside of the delivery sheath 200, or retraction of delivery sheath 200 to expase expandable region 102, may result in a biased eversion whereby a memory shape alloy material comprises at least part of expandable region 102 and results in expansion and eversion when delivery sheath 200 constraints are removed.

In order to obtain the lowest delivery profile, it is noted that in FIG. 5C, 4 layers of material must be collapsed and delivered through the introducer sheath which may increase the diameter of the device and of the required introducer sheath. Accordingly, another embodiment is provided in FIG. 5D which provides a flattening of the expanded device of FIG. 5B. In this case, the flattened collapsed device may lengthen in comparison with its expanded length. In other embodiments, the collapsed and expanded lengths may be approximately equal.

A significant feature of the device 100 of FIG. 5B comprises the expandable region gradually increasing in diameter from a non-expandable proximal region 122 to optimize the incoming blood flow that ultimately reaches the impeller assembly 121 located within the non-expandable proximal region 122. Thus, as seen in FIG. 5B, the distal diameter of the expandable region 102 is larger than the proximal diameter of the expandable region 102 and in the embodiment shown the expandable region 102 includes the inlet apertures 150 though certain alternate embodiments comprise a distal non-expandable region 108 to include the inlet apertures 150 located distal to the expandable region 102.

Thus, in cross-sectional profile, the expanded region 102 may comprise the shape and profile of a truncated or partial cone or elliptical shape, though alternate profile shapes may also be employed.

Turning to FIGS. 6A-6C, an alternative embodiment is provided with an expanded cone profile with the base of the cone comprising the distal end of the expanded expandable region 102. FIG. 5B illustrates the expanded working configuration achieved upon translation distally out of the lumen of the introducer sheath or catheter. FIGS. 6A and 6B illustrate methods to collapse the expandable region 102 of FIG. 6B. Thus, FIG. 6A provides for a folding or a rolling or a furling of the distal edges of the expandable region 102 to a point wherein the external diameter of the folded or rolled expandable region 102 is substantially equal to that of the proximal non-expandable region 122. FIG. 6C illustrates a folding embodiment wherein expandable region 102 is folded back distally so that a 2-layer fold around the circumference of device 100 is achieved.

Once the collapsed expandable region 102 is released from the delivery catheter 200, the impeller may be run in retrograde to force blood through the distal end and cause the rolled or folded distal edges of the expandable region 102 to unfurl and expand to the configuration of FIG. 6B. Alternatively, the expandable region 102 of FIG. 6B may be collapsed and folded in one or more locations to enable the region 102 to fit within the lumen of a delivery catheter or introducer sheath. Accordingly, one or more locations along the expandable region 102 may be weakened or provided with a hinging mechanism to enable folding in the required location(s). Moreover, a shape memory alloy material may comprise at least part of expandable region 102 and that is biased to expand and unfold, unroll and/or unfurl when released from the delivery catheter 200. Expansion occurs as a result of the expansion bias force automatically when the collapsed region 102 is released from the lumen of the delivery catheter or introducer sheath.

The smoothly sloping increase from proximal to distal of the expanded expandable region 102 is useful when the procedure is complete to assist in recollapsing and recapturing the expandable region 102 within the lumen of the introducer sheath or delivery catheter.

With reference now to FIG. 7, another mechanism to retain a collapsed expandable region 102 is provided. There, a retention cap 170 is provided on the distal end of the collapsed expandable region 102, wherein the retention cap 170 serves to hold the expandable region in the desired collapsed configuration. The retention cap 170 may be removed by a number of mechanisms when expansion of expandable region 102 is desired. For example, a push wire or the guide wire may be used to push the cap 170 off its connection points. Alternatively, interference with the rotating impeller assembly 121 may cause the cap 170 to disconnect. Still more alternatively, the cap 170 may be held in place by the delivery catheter 200 and when the cap 170 extends outside the delivery catheter 200, cap 170 is no longer held in place. When the retention cap 170 is removed, the expandable region 102 is free to assume its biased expanded working configuration. The retention cap 170 may be remain connected to the working device by a tether after it is removed from the retention position on the expandable region 102 and/or may comprise a material dissolvable on contact with blood which may serve as the release mechanism for the cap 170 as well. When retention cap 170 is removed and expandable region 102 therefore unconstrained and free to expand, any of the expansion embodiments described herein may be achieved.

Figure 8A:
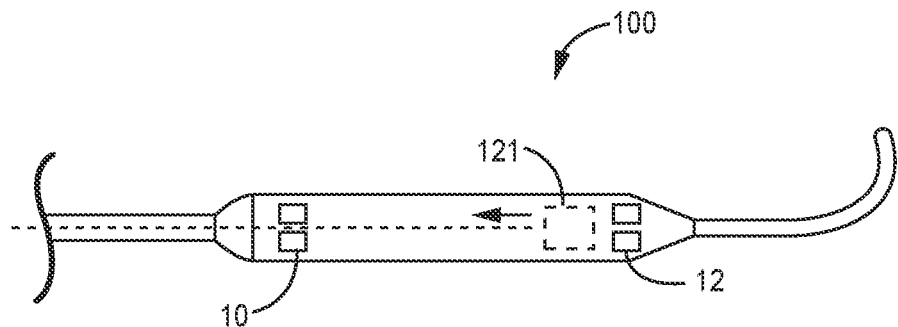
FIG. 8A is a side cutaway view of one embodiment of the present invention.
Figure 8B:
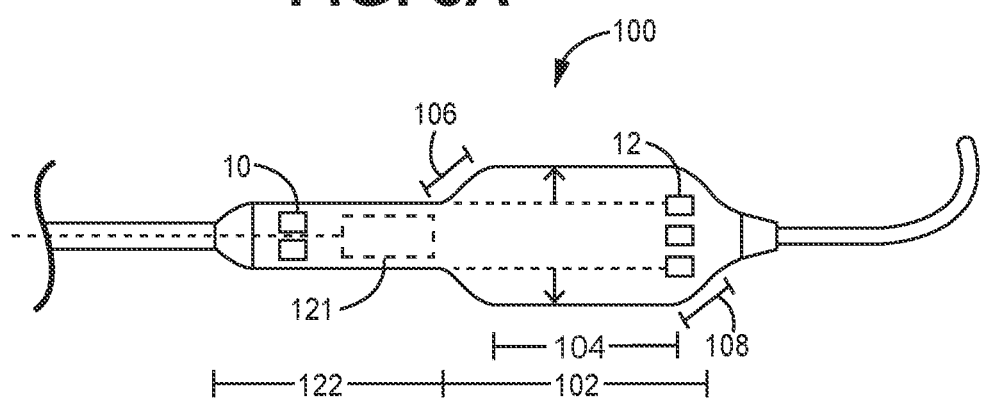
FIG. 8B is a side cutaway view of one embodiment of the present invention.

Turning now to FIGS. 8A and 8B, an expandable region 102 is provided that may comprise, as shown in FIG. 8B, a substantially cylindrical expandable central section 104 with conical transition sections 106, 108 on either side. In this embodiment, the impeller assembly 121 may be engaged with or locked onto a portion of the support structure 130 or in certain cases the outlet apertures. The impeller assembly 121 may, therefore, be advanced distally to the engagement point wherein the expandable region 102 is collapsed to enable the engagement or connection with the impeller assembly 121. The impeller assembly 121 may disengage from the expandable region's support structure or other structure by either pulling the impeller assembly 121 proximally through the housing 14 and/or by rotating the impeller assembly 121. When the impeller assembly 121 is disengaged from its engagement with the support structure or outlet apertures, the expandable region 102 is free to expand according to its bias.

In the embodiment illustrated in FIGS. 8A and 8B, the proximal transition section 106 may, therefore, comprise a diameter that increase in the distal direction and the distal transition section 108 may comprise a diameter that decreases in the distal direction. In these embodiments, the proximal transition section 106 will abut or is adjacent to the distal end of the proximal non-expandable region 122 and the distal transition section 108 abuts or is adjacent to the proximal end of the distal non-expandable region (when present). The transition section(s) 106, 108 may be fixed to the adjacent non-expandable region(s) 122, 124 or one or both of the transition sections 106, 108 may be connected to the adjacent non-expandable region in a way that allows a degree of relative rotation therebetween. The transition sections 106, 108 of this embodiment comprise a profile slope that is between 0 and 90 degrees, wherein the profile slope of the proximal transition section 106 may be substantially equal to the profile slope of the distal transition section 108 or the profile slopes of the proximal and distal transition sections 106, 108 may differ from each other.

The central expandable section 104 may, as shown in FIG. 8B, comprise a cylindrical shape or, alternatively, an elliptical shape. These shapes are merely exemplary.

Because the expandable region 102 in the expanded configuration in the Figures is larger in diameter than the proximal non-expandable region 122, the area and volume are also larger in the expandable region 102, wherein the expandable region 102 is substantially filled with inflowing blood. Subjecting the blood flowing from the expandable region 102 to the smaller fixed diameter, area and volume provided by the proximal non-expandable area 122 results in a higher velocity flow rate at a point that is just distal to the impeller assembly 120.

In certain embodiments of the proximal and/or distal transition sections 106, 108 may comprise a support structure comprising a series of non-linear, but uniformly non-linear, connecting structures comprising, e.g., interconnected stent cells, and or wire struts, that may comprise a geometry that assists in the efficient collapsing of the expandable region 102 to a predictable collapsed configuration that is the smallest possible form without unpredicted interaction between the stent cells or wire struts in the transition sections 106, 108. Accordingly, connecting structures comprising wires or struts 130 in the transition regions 106, 108 may be arranged in a swirl or spiral, or other complementary geometric pattern to allow easy expansion and collapsing, with maximum expansion and minimum collapsing, wherein the struts comprise complementary geometric shapes with smooth peaks and valleys that allow relatively close nesting together of adjacent struts when collapsed or crimped together. In this arrangement, the transition section struts or wires will, upon application of a collapsing or crimping force that overcomes the prevalent biasing expansion force, begin to collapse.

Figure 9A:
FIG. 9A is an end view of one embodiment of the present invention.
Figure 9B:
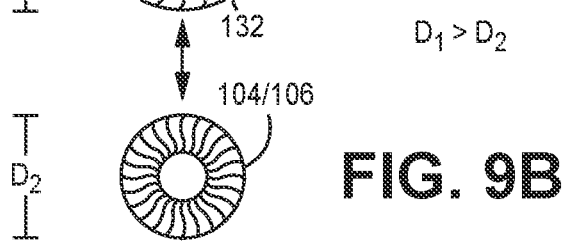
FIG. 9B is an end view of one embodiment of the present invention.

The complementary and/or nesting geometry of the connecting structures 132 enables adjacent connecting structures 132 to collapse against each other in a nested configuration to provide the lowest collapsed profile possible and one with high predictability. This is best shown in FIGS. 9A and 9B where an end view of an exemplary transition section is shown in expanded and collapsed view.

The terms "nest", "nested" or "nesting" are defined herein to mean that the connecting structures 130 are shaped and arranged such that they can be in very close and complementary proximity when the expanded region is in the collapsed or delivery configuration and are separated and/or spaced apart from, and/or without substantial contact, with each other when in the expanded or working configuration.

It will now be apparent that in the case of a device comprising stent cells in the proximal and distal transition sections 106, 108 may not necessarily also comprise stent cells in the central expandable section 104. This central section 104 may comprise an expandable material and, because of the biasing forces provided by the transitions sections, may expand concomitantly with the transition sections without also specifically comprising a biasing expansion force. Thus, the biasing force of the transition sections 106, 108 may force the central section 104 to expand, which may comprise interwoven or interconnected wires or other structure that may form cells or other expandable material, e.g., a polymer including but not limited to a polymer jacket or sleeve, and that can move between collapsed and expanded configurations but that is not biased to expand or collapse. Alternatively, the central section 104 may also be biased to expand, with a comparable biasing force, with a greater biasing force or with a lesser biasing force than the biasing force of the transition regions 106, 108.

In each case described herein, at least part of expandable region 102 may comprise a support structure 130 that may, e.g., comprise a biased-to-expand stent, to achieve the expanded configuration and, in some cases may also comprise connecting structures 132 for transition section expansion as described herein.

The description of the invention and is as set forth herein is illustrative and is not intended to limit the scope of the invention. Features of various embodiments may be combined with other embodiments within the contemplation of this invention. Variations and modifications of the embodiments disclosed herein are possible and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention claimed is:

1. A blood pump having a housing, inlet apertures, outlet apertures and further comprising:
   an impeller assembly comprising at least a rotatable rotor within the housing;
   a collapsible and expandable region disposed distal of the impeller assembly;
   a non-expandable region proximal of the collapsible and expandable region, wherein the collapsible and expandable region comprises a distal portion of the housing comprising the inlet apertures deformed to invert proximally within itself to achieve an inverted collapsed configuration and adapted to translate through a delivery catheter, and wherein the distal portion of the housing is adapted to passively evert to achieve an expanded configuration when the distal portion of the housing comprising the inlet apertures is translated distally out of the delivery catheter and into a target location within a patient's body.

2. The blood pump of claim 1, wherein the collapsible and expandable region comprises a shape memory material.

3. The blood pump of claim 2, wherein the shape memory material comprises a metal and/or a polymer.

4. The blood pump of claim 1, wherein the collapsible and expandable region is biased to evert to achieve the expanded configuration.

5. The blood pump of claim 1, wherein the collapsible and expandable region is biased to expand to achieve the expanded configuration.

6. The blood pump of claim 1, wherein the collapsible and expandable region comprises a cylindrical or elliptical or conical shape.

7. The blood pump of claim 1, wherein the collapsible and expandable region comprises four layers when deformed in the inverted collapsed configuration.

8. The blood pump of claim 1, wherein the collapsible and expandable region comprises two layers when in the expanded configuration.

9. The blood pump of claim 1, wherein the collapsible and expandable region comprises a support structure comprising an expandable stent.

10. The blood pump of claim 9, wherein the expandable stent is covered by a polymer.

11. The blood pump of claim 1, wherein the collapsible and expandable region comprises a distal portion of the housing deformed to roll proximally upon itself to achieve the inverted collapsed configuration.

12. The blood pump of claim 11, wherein the distal portion of the housing is adapted to unroll to achieve the expanded configuration.

13. The blood pump of claim 11, wherein the collapsible and expandable region comprises a shape memory material, and wherein the collapsible and expandable region is biased to unroll and expand to achieve the expanded configuration.

14. The blood pump of claim 1, further comprising:
    a retention cap detachably attached to the collapsible and expandable region, wherein the retention cap deforms the collapsible and expandable region into the inverted collapsed configuration, wherein the collapsible and expandable region is biased to expand and to achieve the expanded configuration when the retention cap is detached therefrom.

15. The blood pump of claim 1,
    wherein the impeller assembly is detachably attached to the collapsible and expandable region to deform the collapsible and expandable region into the inverted collapsed configuration, wherein detachment of the impeller assembly from the collapsible and expandable region results in the collapsible and expandable region achieving the expanded configuration.

16. The blood pump of claim 15, wherein the collapsible and expandable region comprises a support structure comprising an expandable stent.

17. The blood pump of claim 16, wherein the collapsible and expandable region comprises a central expandable region and proximal and distal transition sections, wherein the proximal and distal transition sections comprise connecting struts that are adapted to nest together when the collapsible and expandable region is collapsed.

* * * * *